United States Patent
Allen et al.

(10) Patent No.: US 10,614,918 B2
(45) Date of Patent: Apr. 7, 2020

(54) AUTHENTICATION OF MEDICATION DELIVERY VEHICLE TO FACILITATE MEDICATION RELEASE

(71) Applicant: International Business Machines Corporation, Armonk, NY (US)

(72) Inventors: Ira L. Allen, Dallas, TX (US); Gregory J. Boss, Saginaw, MI (US); Lawrence A. Clevenger, Rhinebeck, NY (US); Andrew R. Jones, Round Rock, TX (US); Kevin C. McConnell, Austin, TX (US); John E. Moore, Jr., Brownsburg, IN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 389 days.

(21) Appl. No.: 15/494,796

(22) Filed: Apr. 24, 2017

(65) Prior Publication Data
US 2018/0307798 A1  Oct. 25, 2018

(51) Int. Cl.
G16H 40/63 (2018.01)
G16H 20/13 (2018.01)
A61K 9/48 (2006.01)

(52) U.S. Cl.
CPC ........... *G16H 40/63* (2018.01); *A61K 9/4808* (2013.01); *G16H 20/13* (2018.01)

(58) Field of Classification Search
CPC ....... G16H 40/63; G16H 20/13; A61K 9/4808
See application file for complete search history.

(56) References Cited

U.S. PATENT DOCUMENTS

| | | | |
|---|---|---|---|
| 8,760,636 B2 | 6/2014 | Knopp et al. | |
| 9,659,423 B2* | 5/2017 | Robertson | A61B 5/0006 |
| 10,251,553 B2* | 4/2019 | Kozloski | A61M 31/00 |
| 2013/0181046 A1 | 7/2013 | Fedorko et al. | |
| 2013/0345505 A1* | 12/2013 | Trovato | A61B 5/411 600/104 |
| 2014/0051965 A1* | 2/2014 | Zdeblick | A61B 5/0028 600/407 |
| 2015/0343144 A1* | 12/2015 | Altschul | H05K 999/99 604/503 |

OTHER PUBLICATIONS van der Schaar et al., A novel ingestible electronic drug delivery and monitoring device, 2013, Gastrointestinal Endoscopy, vol. 78, No. 3, pp. 520-528. (Year: 2013).*

(Continued)

*Primary Examiner* — Christopher L Gilligan
*Assistant Examiner* — C. Luke Gilligan
(74) *Attorney, Agent, or Firm* — Garg Law Firm, PLLC; Rakesh Garg; Scott Dobson (57) ABSTRACT

A delivery device includes a circuit for receiving an authentication signal. The delivery device contains a substance encapsulated therein. The delivery device determines whether a user is authenticated based upon the authentication signal and an identifier stored within the delivery device. The delivery device heats, responsive to determining that the user is not authenticated within a predetermined time period after the delivery device being ingested by the user, the substance encapsulated within the delivery device.

18 Claims, 6 Drawing Sheets

(56) References Cited

OTHER PUBLICATIONS

Anonymously; "RFID pill blister for medicine compliance using visual support"; http://ip.corn/IPCOM/000195120D; Apr. 21, 2010.
Anonymously; "Tailored pill blister to support intelligent and user friendly pill reminder application in mobile device"; http://ip.com/IPCOM/000195114D; Apr. 21, 2010.
IPCOM000034366D; "Anti-counterfeit Authenticity Labels—Smart Chips with Electronic Ink & Wireless I/O—Duplicate Serial Number Detection"; http://ip.com/IPCOM/000034366D; Jan. 19, 2005.

\* cited by examiner

AUTHENTICATION OF MEDICATION DELIVERY VEHICLE TO FACILITATE MEDICATION RELEASE

TECHNICAL FIELD

The present invention relates generally to a method, system, and computer program product for authentication of a medication delivery vehicle. More particularly, the present invention relates to a method, system, and computer program product for authentication of a medication delivery vehicle with a user to facilitate release of medication contained therein.

BACKGROUND

Many medications are expensive to purchase, have significant street value, and are often stolen or otherwise obtained for the purpose of reselling. Additionally, as patients become increasingly memory challenged due to age or illness, health aids, domestic aids, and other service providers may be necessary to assist in administering medications to the patient. For example, the service provider may assist a patient in administering medication in patient's home and/or in an assisted living facility in which the patient resides. Unfortunately, the service provider may substitute a different medication for the intended medication either accidently or purposely in order to keep or sell the medication. This type of abuse often goes unrecognized. Accordingly, a need exists to authenticate a medication to ensure that a patient receives only the medication that has been prescribed to the patient.

Published and web-based reference sheets are available including a number of medications to allow a patient to look up and visually identify a particular medication prior to taking the medication. These reference sheets typically include an image of a particular pill or other medication showing one or more of a shape, color, and marking of the pill. However, looking up the particular medication that the patient has been prescribed is a time consuming process. A typical patient will stop at the color or size, and can be easily convinced that a different looking pill is a new version of the pill even when such may not be the case. In addition, securing medication by locking the medication within a storage requires diligence and introduces the risk of the patient forgetting to take the medication due to the medication no longer being within sight of the patient.

SUMMARY

The illustrative embodiments provide a method, system, and computer program product. An embodiment of a method includes monitoring, by a circuit of a delivery device, for receiving an authentication signal. In the embodiment, the delivery device contains a substance encapsulated therein. In the embodiment, the method further includes determining whether a user is authenticated based upon the authentication signal and an identifier stored within the delivery device. In the embodiment, the method further includes heating, responsive to determining that the user is not authenticated within a predetermined time period after the delivery device being ingested by the user, the substance encapsulated within the delivery device.

An embodiment includes a computer program product. The computer program product includes one or more computer-readable storage devices, and program instructions stored on at least one of the one or more storage devices.

An embodiment includes a computer system. The computer system includes one or more processors, one or more computer-readable memories, and one or more computer-readable storage devices, and program instructions stored on at least one of the one or more storage devices for execution by at least one of the one or more processors via at least one of the one or more memories.

BRIEF DESCRIPTION OF THE DRAWINGS

Certain novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

The illustrative embodiments described herein generally relate to a method, system, and computer program product for authentication of a medication delivery vehicle (MDV) with a user to facilitate release of medication contained therein. In one or more embodiments, a medication delivery vehicle (MDV) containing a medication encapsulated therein is provided. In one or more embodiments, a medication delivery vehicle (MDV) is a delivery device or container configured to contain a medication or other substance for dispensing to a user when the MDV is ingested by the user. In particular embodiments, the MDV is in a pill or capsule form. In one or more embodiments, when the MDV is consumed by a patient, the MDV is wirelessly authenticated to an authentication device associated with the patient, and the MDV allows the medication to be released into the patient's digestive tract to produce the desired effect upon the patient. In particular embodiments, the MDV utilizes radio frequency identification (RFID) tag and scanner wireless technology to authenticate the MDV with the authentication device.

In one or more embodiments, if the MDV fails to authenticate, or a suitable authentication mechanism is not used with the MDV within a predefined period of ingesting the MDV, the MDV either remains intact without dispensing the medication contained therein, or triggers a neutralizing process to alter the chemical structure of the medication to neutralize or otherwise reduce the effectiveness of the medication encapsulated within the MDV.

In a particular embodiment, a processor of the MDV triggers a capacitor to release an electrical current to an electrically resistive mesh pouch containing the medication if the MDV fails to be authenticated. In the particular embodiment, the release of the electrical current to the mesh pouch causes heating of the mesh pouch and the medication contained therein to a suitable temperature for a suitable time period resulting in neutralization of and/or reduction in the effectiveness of the medication. In one or more embodiments, the temperature is low enough and the time period is short enough such that the patient is not negatively affected by the neutralization process, yet the temperature is high enough and the duration long enough to effectively neutralize the medication to a sufficient degree. Guidance from pharmaceutical manufacturers recommend that most of the manufacturer's products be stored at a controlled room temperature of 68 degrees to 77 degrees Fahrenheit (F), and that degradation may occur for products stored above 86 degrees F. In a particular embodiment, the mesh pouch is heated to a temperature of 108 degrees Fahrenheit (F) for several seconds to render the medication inert and/or reduce the effectiveness of the medication contained within the mesh pouch.

Upon neutralization and/or reduction in effectiveness of the medication due to lack of authentication of the MDV, the medication has little or no effect on the patient. Within the scope of the illustrative embodiments, neutralization of a medication includes a reduction in the effectiveness of the medication. In one or more embodiments, regardless of whether the MDV is authenticated, any undigested components of the MDV are safely passed from the patient's digestive system.

In one or more embodiments, an MDV including a prescribed medication is provided to a user, such as a patient, to whom the medication is prescribed. In a particular embodiment, the MDV includes an RFID circuit configured to store a unique RFID public key or other identifier associated with the user. In a particular embodiment, a medication provider, such as a pharmacy, encodes the RFID circuit of the MDV with the unique public RFID associated with the user prior to providing the MDV to the user.

In one or more embodiments, the user has an authentication device, such as an RFID device, that is configured to transmit a unique private key, such as a unique private RFID key, or another type of code related to the identifier of the MDV. In a particular embodiment, the authentication device is worn by the user, such as in a non-limiting watch form-factor. In another particular embodiment, the authentication device is implanted within the body of the user.

In one or more embodiments, the MDV has an outer layer dissolvable by a fluid or substance present in the human body, such as saliva, that coats, covers, or otherwise contacts an external surface of the MDV. In the embodiment, an inner layer under the outer layer includes a plurality of electrical contacts in communication with an electronic circuit of the MDV. In the embodiment, the MDV includes an isolated mesh pouch storing the medication. In particular embodiments, the mesh pouch is constructed of an electrically resistive material such as an electrically resistive refractory or inert/non-reactive metal. In the embodiment, the circuit is electrically connected with one or more capacitors coupled to the mesh pouch. In one or more embodiments, the one or more capacitors are configured to store a charge to be provided to the mesh pouch in response to a signal from the circuit.

In an example operation of the MDV, a user places the MDV in the user's mouth and swallows the MDV. The outer layers of the MDV is dissolved by saliva within the user's mouth and digestive track within a short period of time such as several seconds. Upon dissolving of the outer layer, saliva or another fluid makes an electrically conductive path connecting the electrical contacts disposed on the inner layer. The connecting of the contacts closes an electrical circuit indicating that the MDV has been ingested by the user.

In a particular embodiment, the closed circuit between the electrical contacts triggers the start of an internal timer within the circuit of the MDV. In another particular embodiment, the MDV includes a separate timer circuit. Upon start of the timer, the wireless circuit of the MDV interrogates the authentication device for the private RFID key or another type of code associated with the user. In one embodiment, the circuit passively waits for a signal from the authentication device.

If the wireless circuit receives the private key or another user-specific code from the authentication device, and the circuit authenticates the private key or code with the public key or identifier stored within the circuit within a predetermined time period, the circuit stops the timer prior to the timer expiring. After a period of time after the timer has stopped, stomach acids within the stomach of the user dissolve the mesh pouch thereby releasing the medication within the body of the user. As a result, the user receives the full benefits of the medicine.

However, if the circuit does not receive the private key or code from the authentication device and/or does not authenticate the private key or code with the public key or identifier stored within the circuit within the predetermined time period the timer expires. Responsive to the timer expiring, the circuit triggers the one or more capacitors to discharge a current into the mesh pouch. In response, the mesh pouch heats up to above a threshold temperature, for example 108 degree Fahrenheit or greater, for at least a threshold period of time, for example five seconds or more, to neutralize and/or reduce the effectiveness of the medication stored within the mesh pouch. As a result, the medication is rendered fully or partially ineffective to the user.

Some embodiments provide for a system to ensure that medication is only fully effective on the patient for whom the medication is designated. In particular embodiments, e.g., when the medication is stolen or taken by someone other than the intended patient, the medication is neutralized before release, thus eliminating the efficacy of the medication and causing little or no reaction in the patient. In some embodiments, prescription drug thefts may be reduced and it can be ensured that the intended patient (e.g., an elderly person being cared for by another) will receive the medication.

The illustrative embodiments are described with respect to certain types of medication delivery vehicles, pills, medications, keys, codes, identifiers, RFID technology, wireless technology, contents, transmissions, responses, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

For example, while some embodiments are described with respect to RFID technology, an embodiment may be adapted to use another suitable wireless communication technology within the scope of the embodiments. As another example, an embodiment may be adapted to use another suitable sonic, ultrasound, infrared, or other types of signals to trigger the circuit in the MDV in a similar manner, and such adaptations are contemplated within the scope of the illustrative embodiments. Any suitable pair of coded data can be used in place of the RFID keys, identifiers, or codes described herein.

Furthermore, the illustrative embodiments may be implemented with respect to any type of data, data source, or access to a data source over a data network. Any type of data storage device may provide the data to an embodiment of the invention, either locally at a data processing system or over a data network, within the scope of the invention. Where an embodiment is described using a mobile device, any type of data storage device suitable for use with the mobile device may provide the data to such embodiment, either locally at the mobile device or over a data network, within the scope of the illustrative embodiments.

The illustrative embodiments are described using specific code, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable mobile devices, structures, systems, applications, or architectures therefor, may be used in conjunction with such embodiment of the invention within the scope of the invention. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 1:
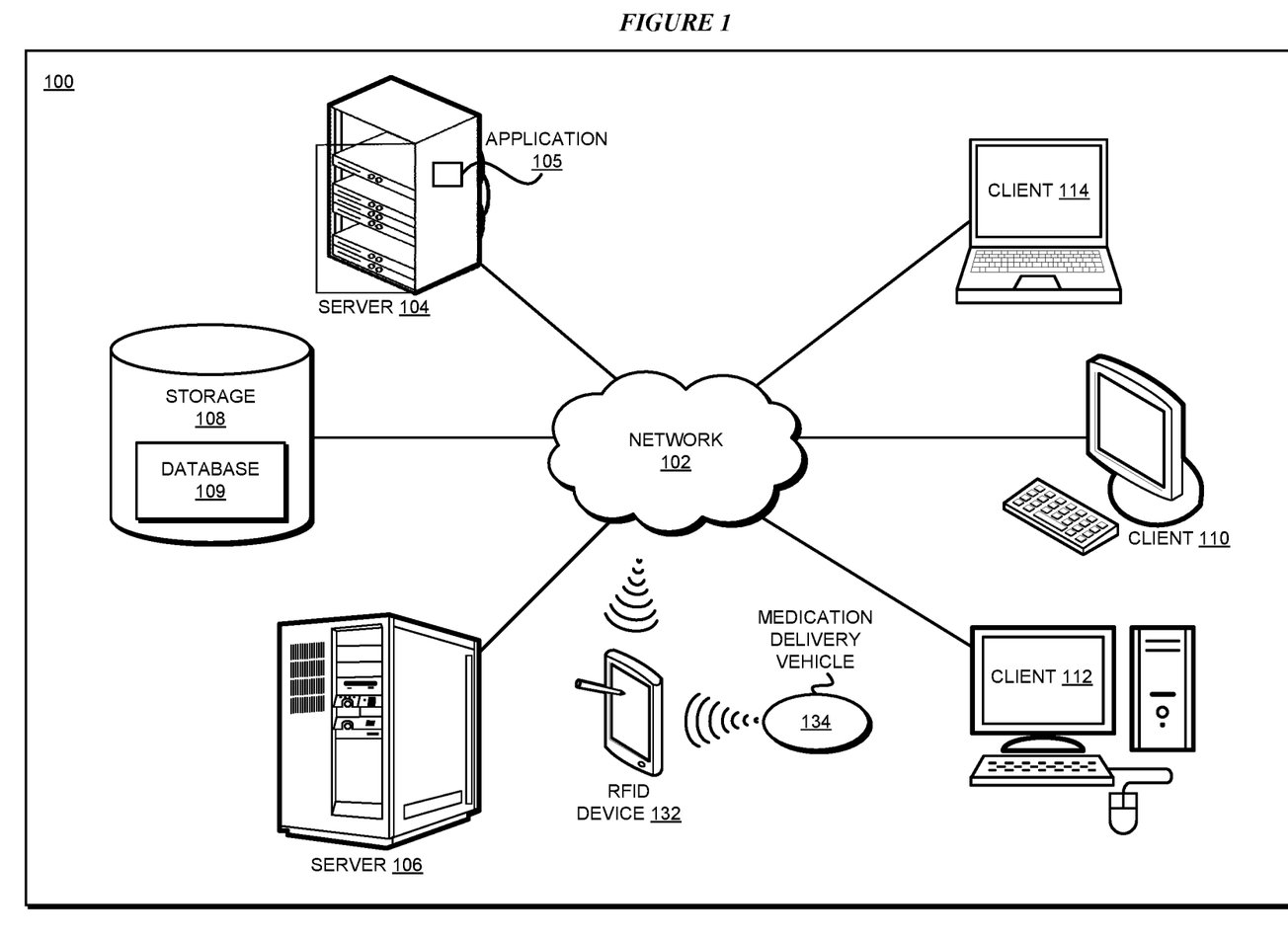
FIG. 1 depicts a block diagram of a network of data processing systems in which illustrative embodiments may be implemented.
Figure 2:
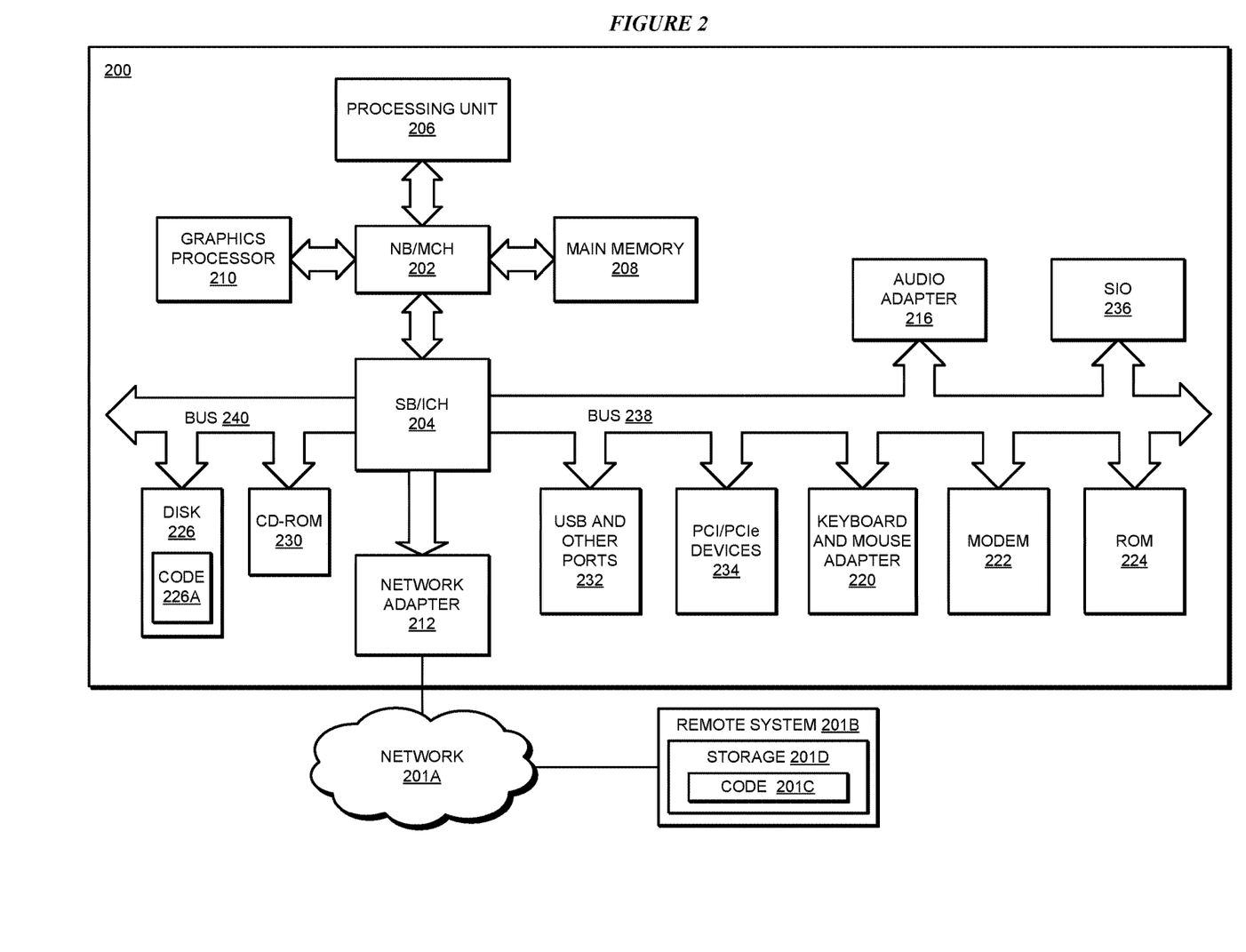
FIG. 2 depicts a block diagram of a data processing system in which illustrative embodiments may be implemented.

With reference to the figures and in particular with reference to FIGS. 1 and 2, these figures are example diagrams of data processing environments in which illustrative embodiments may be implemented. FIGS. 1 and 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network 102. Network 102 is the medium used to provide communications links between various devices and computers connected together within data processing environment 100. Network 102 may include connections, such as wire, wireless communication links, or fiber optic cables.

Clients or servers are only example roles of certain data processing systems connected to network 102 and are not intended to exclude other configurations or roles for these data processing systems. Server 104 and server 106 couple to network 102 along with storage unit 108. Software applications may execute on any computer in data processing environment 100. Clients 110, 112, and 114 are also coupled to network 102. A data processing system, such as server 104 or 106, or client 110, 112, or 114 may contain data and may have software applications or software tools executing thereon.

Only as an example, and without implying any limitation to such architecture, FIG. 1 depicts certain components that are usable in an example implementation of an embodiment. For example, servers 104 and 106, and clients 110, 112, 114, are depicted as servers and clients only as example and not to imply a limitation to a client-server architecture. As another example, an embodiment can be distributed across several data processing systems and a data network as shown, whereas another embodiment can be implemented on a single data processing system within the scope of the illustrative embodiments. Data processing systems 104, 106, 110, 112, and 114 also represent example nodes in a cluster, partitions, and other configurations suitable for implementing an embodiment.

RFID device 132 is an example of an authentication device described herein. For example, RFID device 132 can take the form of a smartphone, a tablet computer, a laptop computer, client 110 in a stationary or a portable form, a wearable computing device, or any other suitable device. Any software application described as executing in another data processing system in FIG. 1 can be configured to execute in RFID device 132 in a similar manner. Any data or information stored or produced in another data processing system in FIG. 1 can be configured to be stored or produced in RFID device 132 in a similar manner.

Medication delivery vehicle (MDV) 134 is an example of a medication delivery vehicle (MDV) described herein containing a medication to be dispensed to a user, such as a patient, that has ingested MDV 134.

Application 105 implements an embodiment described herein in the manner of a remote server-based application or service. Application 105 may store patent prescription information locally, or use storage unit 108 that is accessible over network 102 to store patient prescription information in a secure manner within database 109.

Servers 104 and 106, storage unit 108, and clients 110, 112, and 114, and RFID device 132 may couple to network 102 using wired connections, wireless communication protocols, or other suitable data connectivity. Clients 110, 112, and 114 may be, for example, personal computers or network computers.

In the depicted example, server 104 may provide data, such as boot files, operating system images, and applications to clients 110, 112, and 114. Clients 110, 112, and 114 may be clients to server 104 in this example. Clients 110, 112, 114, or some combination thereof, may include their own data, boot files, operating system images, and applications. Data processing environment 100 may include additional servers, clients, and other devices that are not shown.

In the depicted example, data processing environment 100 may be the Internet. Network 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such as servers 104 and 106, or clients 110, 112, and 114 in FIG. 1, or another type of device in which computer usable program code or instructions implementing the processes may be located for the illustrative embodiments.

Data processing system 200 is also representative of a data processing system or a configuration therein, such as data processing system 132 in FIG. 1 in which computer usable program code or instructions implementing the processes of the illustrative embodiments may be located. Data processing system 200 is described as a computer only as an example, without being limited thereto. Implementations in the form of other devices, such as device 132 in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to NB/MCH 202 through an accelerated graphics port (AGP) in certain implementations.

In the depicted example, local area network (LAN) adapter 212 is coupled to South Bridge and I/O controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and I/O controller hub 204 through bus 238. Hard disk drive (HDD) or solid-state drive (SSD) 226 and CD-ROM 230 are coupled to South Bridge and I/O controller hub 204 through bus 240. PCI/PCIe devices 234 may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and I/O controller hub (SB/ICH) 204 through bus 238.

Memories, such as main memory 208, ROM 224, or flash memory (not shown), are some examples of computer usable storage devices. Hard disk drive or solid state drive 226, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 105 and 134 in FIG. 1, are located on storage devices, such as in the form of code 226A on hard disk drive 226, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory 224, or in one or more peripheral devices.

Furthermore, in one case, code 226A may be downloaded over network 201A from remote system 201B, where similar code 201C is stored on a storage device 201D. in another case, code 226A may be downloaded over network 201A to remote system 201B, where downloaded code 201C is stored on a storage device 201D.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub 202. A processing unit may include one or more processors or CPUs.

The depicted examples in FIGS. 1-2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and disk 226 is manifested as a virtualized instance of all or some portion of disk 226 that may be available in the host data processing system. The host data processing system in such cases is represented by data processing system 200.

Figure 3:
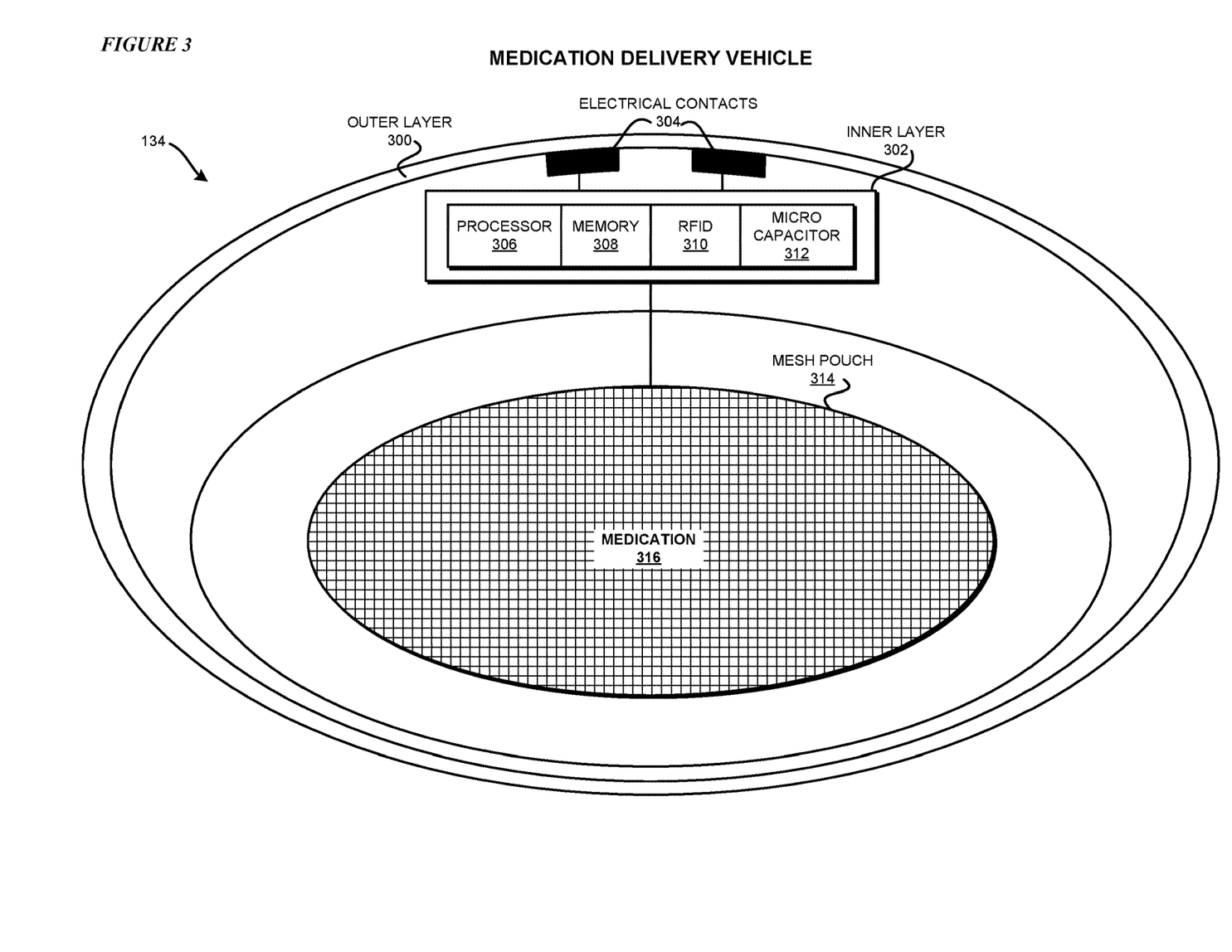
FIG. 3 depicts a block diagram of an embodiment of a medication delivery vehicle (MDV) in accordance with an illustrative embodiment.

With reference to FIG. 3, this figure depicts a block diagram of an embodiment of a medication delivery vehicle (MDV) 134 in accordance with an illustrative embodiment. MDV 134 includes an outer layer 300 configured to be dissolvable by saliva that coats and/or covers an external surface of MDV 134. In a particular embodiment, outer layer 300 is configured to cover the entire outer surface of MDV 134. In still another embodiment, outer layer 300 may be configured to cover a portion of the outer surface of MDV 134. MDV 134 further includes an inner layer 302 under outer layer 300. Inner layer 302 includes a plurality of electrical contacts 304 disposed upon and/or within inner layer 302. Electrical contacts 304 are in communication with a processor 306. Processor 304 is in further communication with a memory 308. In particular embodiments memory 308 is configured to store one or more program instructions executable by processor 306 to perform one or more of the functions of MDV 134 described herein.

In the embodiment, processor 306 is in further communication with RFID circuitry 310. In one or more embodiments, RFID circuit 310 is configured to store a public RFID encryption key associated with the user, receive a private RFID encryption key associated with the user from RFID device 132, and authenticate the user using the private RFID encryption key and the public RFID encryption key. Processor 306 is further in communication with a micro capacitor 312, and micro capacitor 312 is in further communication with a mesh pouch 314. In one or more embodiments, micro capacitor 312 is configured to store a charge current to be provided to mesh pouch 314 in response to a signal from processor 306. In particular embodiments, micro capacitor 312 may include one or more of a graphine micro supercapacitor; a RuO2, Fe2O3, IrO2, TiS2 capacitor; or a lithium doped carbon nanotube capacitor. In one or more embodiments, processor 306, memory 308, RFID circuitry 310, and micro capacitor 312 are disposed upon a surface of or within inner layer 302. In an alternative embodiment, processor 306, memory 308, RFID circuitry 310, and micro capacitor 312 can be disposed within an interior portion of MDV 134. In at least one embodiment, processor 306, memory 308, RFID circuitry 310, and micro capacitor 312 are integrated together as a single component. In alternative embodiments, one or more of processor 306, memory 308, RFID circuitry 310, and micro capacitor 312 can be separate components.

In one or more embodiments, mesh pouch 314 contains a medication 316 encapsulated therein. In particular embodiments, mesh pouch 314 is constructed of an electrically resistive material such as an electrically resistive, refractory, inert/non-reactive metal. In still other particular embodiments, mesh pouch 314 may be constructed of an electrically conductive material. In particular embodiments, mesh pouch 314 may include a mesh of capillaries containing medication 316. In one or more embodiments, mesh pouch 314 is configured to receive an electrical current from micro capacitor 312 causing heating of mesh pouch 314 and medication 316 contained therein to a predetermined temperature for a predetermined time period resulting in neutralization of and/or reduction in the effectiveness of the medication. Although the embodiment illustrated in FIG. 3 is shown with processor 306, memory 308, RFID circuit 310, and micro capacitor 312 within an interior of MDV 134, in other embodiments one or more of processor 306, memory 308, RFID circuit 310, and micro-capacitor 312 can be disposed on inner layer 302 or a surface of MDV 134.

Figure 4:
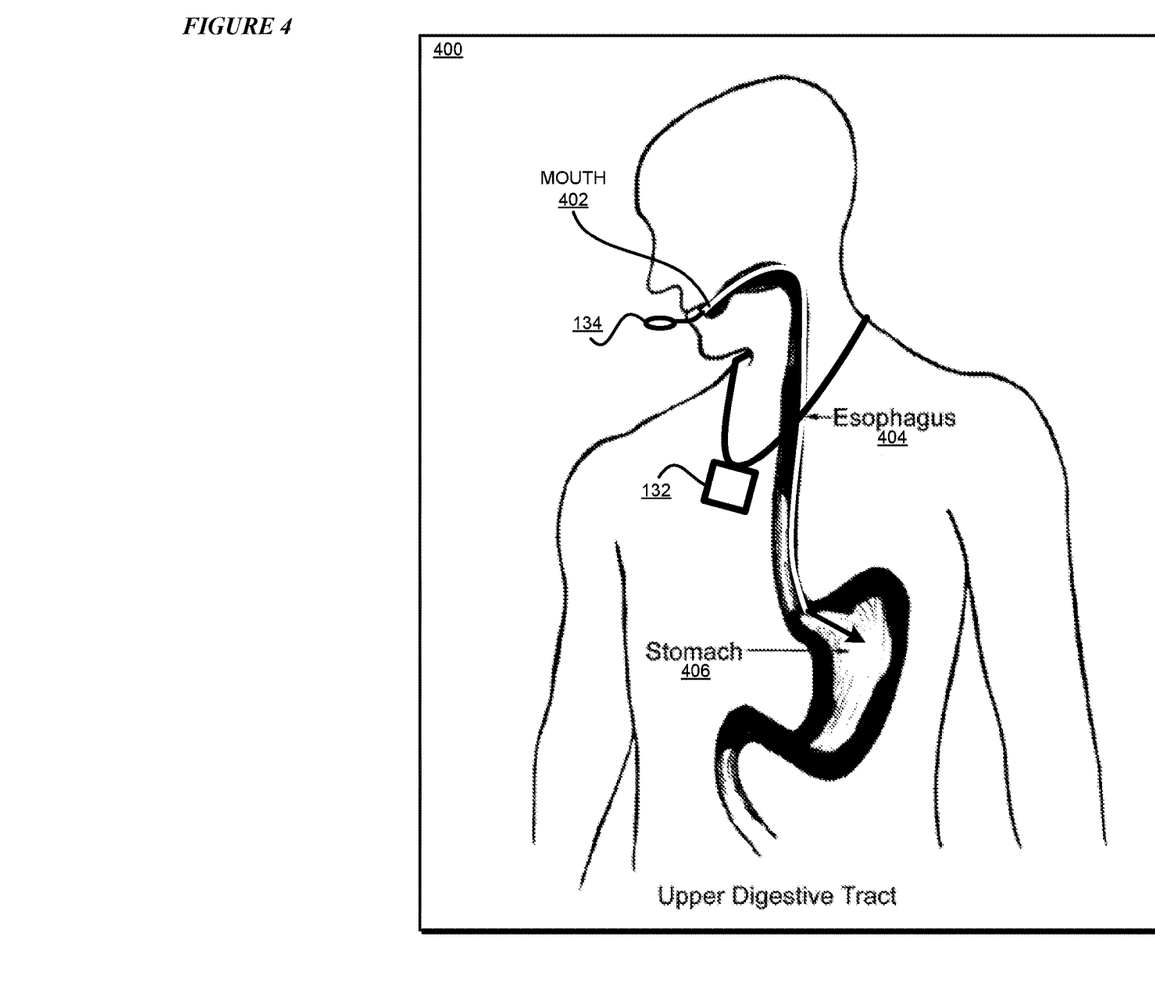
FIG. 4 depicts a block diagram of an example scenario for authentication of a medication delivery vehicle (MDV) within a simplified upper digestive tract of a user in accordance with an illustrative embodiment.

With respect to FIG. 4, this figure depicts a block diagram of an example scenario for authentication of a medication delivery vehicle (MDV) within a simplified upper digestive tract 400 of a user in accordance with an illustrative embodiment. Upper digestive tract 400 includes a mouth 402, an esophagus 404, and a stomach 406. In the embodiment illustrated in FIG. 4, the user is wearing an RFID device 132 upon the body of a user. In the particular embodiment, RFID device 132 is in a necklace and/or pendant form for wearing around a neck of the user. In other embodiments, RFID device 134 is worn on an arm or wrist of the user. In still other embodiments, RFID device 134 is not worn by the user but is instead located nearby to the user during ingestion of MDV 134. In the example scenario, the user ingests an MDV 134 by placing MDV 134 within mouth 402 and swallowing MDV 134 to pass through esophagus 404 to stomach 406. As described herein, saliva within the user's mouth dissolves the outer layer of MDV 134 and activates the electrical contacts of MDV 134 to initiate a timer having a predetermined time period. MDV 134 then attempts to authenticate with RFID device 132. If MDV 134 successfully authenticates with RFID device 132 within the predetermined time period, the timer stops and MDV 134 dissolves within stomach 406 to release the medication contained within MDV 134 into stomach 406.

If MDV 134 is unsuccessful in authenticating with RFID device 132 within the predetermined time period, MDV 134 heats the medication contained within MDV 134 at a predetermined temperature for a predetermined time period to neutralize and/or otherwise reduce the effectiveness of the medication encapsulated within MDV 134 as described herein. In one or more embodiments, any undigested components of MDV 134 are passed through the digestive tract of the user.

Figure 5:
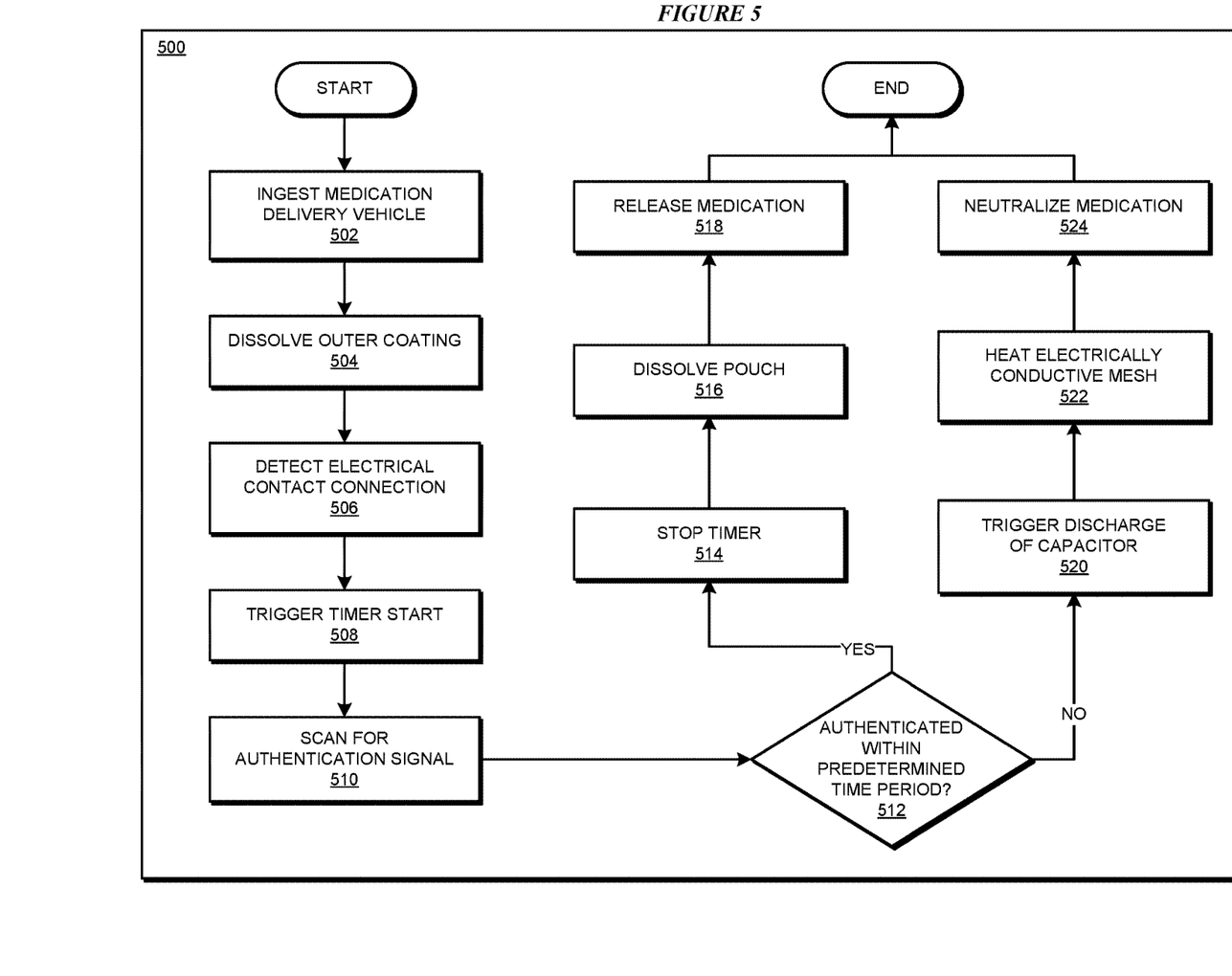
FIG. 5 depicts a flowchart of an example process for authentication of a medication delivery vehicle (MDV) in accordance with an illustrative embodiment.

With respect to FIG. 5, this figure depicts a flowchart of an example process 500 for authentication of a medication delivery vehicle (MDV) in accordance with an illustrative embodiment. In block 502, a user ingests medication delivery vehicle 134. In block 504, saliva of the user dissolves an outer coating such as outer layer 300 of MDV 134. In block 506, processor 306 detects a connection between electrical contacts 304 caused by the saliva of the user. In block 508, processor 306 triggers the start of a timer having a predetermined time period of duration. In block 510, RFID circuit 310 scan for an authentication signal from an authentication device such as RFID device 132. In an alternative embodiment, MDV 134 attempts to authenticate the user with a remote system, such as server 104, of FIG. 1 either directly or through an intermediary device such as RFID device 132.

In block 512, RFID circuit 310 and/or processor 306 determines whether the user is authenticated within the predetermined time period. In particular embodiments, RFID circuit 310 and/or processor 306 authenticates the user using an private RFID encryption key received from RFID device 132 and a public RFID encryption key stored within MDV 134. In a particular embodiment, RFID circuit 310 and/or processor 306 authenticates the user by matching the private encryption key with the public encryption key stored within MDV 134. If the user is authenticated within the predetermined time period, process 500 continues to block 514. In block 512, processor 306 stops the timer. In block 516, mesh pouch 314 of MDV 134 is dissolved within the stomach of the user. In block 518, medication 316 is released into the stomach of the user to be absorbed by the body of the user and process 500 ends.

If in block 512, RFID circuit 310 and/or processor 306 determines that the user is not authenticated within the predetermined time period, processor 306 triggers discharge of an electrical current from micro capacitor 312 to the electrically conductive and/or electrically resistive mesh pouch 314 in block 520. In block 522, mesh pouch 314 heats to a predetermined temperature for a predetermined time period in response to receiving the electrical current from micro capacitor 312. In 524, medication 316 is neutralized and/or reduced in effectiveness pouch. As a result, medication 316 is rendered fully or partially ineffective to the user when dissolved by the stomach of the user. The process 500 then ends.

Figure 6:
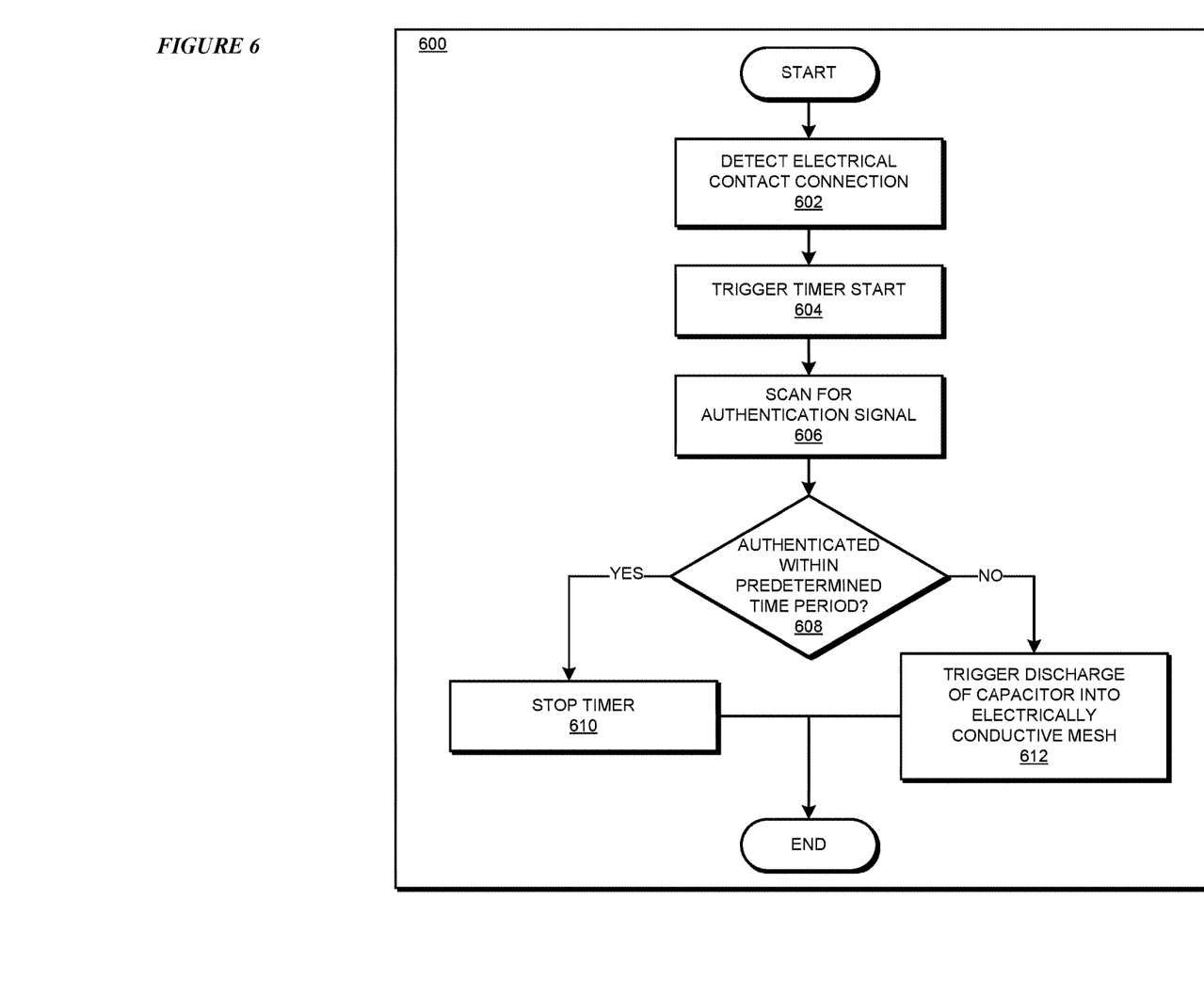
FIG. 6 depicts a flowchart of an example process of a medication delivery vehicle (MDV) for authentication of medication delivery in accordance with an illustrative embodiment.

With respect to FIG. 6, this figure depicts a flowchart of an example process 600 of medication delivery vehicle (MDV) 134 for authentication of a medication delivery in accordance with an illustrative embodiment. In the embodiment of FIG. 6, a user ingests MDV 134 and saliva of the user dissolves outer layer 300 of MDV 134. In block 602, processor 306 detects a connection between electrical contacts 304 caused by the saliva of the user. In block 604, processor 306 triggers the start of a timer having a predetermined time period of duration. In block 608, RFID circuit 310 scan for an authentication signal from an authentication device such as RFID device 132.

In block 608, RFID circuit 310 and/or processor 306 determines whether the user is authenticated within the predetermined time period. In particular embodiments, RFID circuit 310 and/or processor 306 authenticates the user using an private RFID encryption key received from RFID device 132 and a public RFID encryption key stored within MDV 134. If the user is authenticated within the predetermined time period, process 600 continues to block 610. In block 610, processor 306 stops the timer. Accordingly, when mesh pouch 314 of MDV 134 is dissolved within the stomach of the user, medication 316 is released into the stomach of the user to be absorbed by the body of the user and process 600 ends.

If in block 608, RFID circuit 310 and/or processor 306 determines that the user is not authenticated within the predetermined time period, processor 306 triggers discharge of an electrical current from micro capacitor 312 to the electrically conductive and/or electrically resistive mesh pouch 314 in block 612 and the process 600 ends. As a result, mesh pouch 314 heats to a predetermined temperature for a predetermined time period in response to receiving the electrical current from micro capacitor 312, and medication 316 is neutralized and/or reduced in effectiveness pouch.

Accordingly medication 316 is rendered fully or partially ineffective to the user when dissolved by the stomach of the user.

Although various embodiments describe medication as being stored within medication delivery vehicle 134, it should be understood that in other embodiments other types of substances may be stored in a delivery vehicle that is desired to be authenticated with a user before the user may use the substance.

Thus, a computer implemented method, system or apparatus, and computer program product are provided in the illustrative embodiments for authentication of a delivery vehicle with a user to facilitate release of medication or any other substance contained therein and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method comprising:
    monitoring, by a circuit of a delivery device, for receiving an authentication signal, the delivery device containing a substance encapsulated in a mesh;
    determining whether a user is authenticated based upon the authentication signal and an identifier stored within the delivery device; and
    heating, responsive to determining that the user is not authenticated within a predetermined time period after the delivery device being ingested by the user, the mesh and the substance contained therein, the heating including applying an electrical current to the mesh containing the substance for a predetermined amount of time for neutralizing or reducing an effectiveness of the substance.

2. The method of claim 1, wherein determining whether the user is authenticated is performed by a radio frequency identification (RFID) circuit of the delivery device.

3. The method of claim 1, wherein heating of the substance comprises discharging a capacitor into the mesh configured to encapsulate the substance.

4. The method of claim 3, wherein the mesh comprises an electrically conductive mesh.

5. The method of claim 1, wherein determining that the user is not authenticated within the predetermined time period further comprises:
    determining that the delivery device has been ingested by the user; and
    determining that the predetermined time period has elapsed since ingestion of the delivery device without authentication occurring.

6. The method of claim 5, wherein determining that the delivery device has been ingested by the user includes determining that a closed circuit exists between a plurality of electrical contacts of the delivery device.

7. The method of claim 6, wherein the closed circuit is caused by saliva of the user.

8. The method of claim 1, wherein the authentication signal includes a private encryption key associated with the user, and the identifier stored within the delivery device is a public encryption key associated with the user.

9. The method of claim 8, wherein determining whether the user is authenticated includes matching the private encryption key with the public encryption key.

10. The method of claim 1, wherein the authentication signal is received from an authentication device associated with the user.

11. The method of claim 9, wherein the authentication device is configured to be worn by the user or implanted within the user.

12. The method of claim 1, wherein the substance is a medication.

13. A computer usable program product comprising one or more computer-readable non-transitory storage devices, and program instructions stored on at least one of the one or more storage devices, the stored program instructions comprising:
   program instructions to monitor, by a circuit of a delivery device, for receiving an authentication signal, the delivery device containing a substance encapsulated in a mesh;
   program instructions to determine whether a user is authenticated based upon the authentication signal and an identifier stored within the delivery device; and
   program instructions to cause heating, responsive to determining that the user is not authenticated within a predetermined time period after the delivery device being ingested by the user, the mesh and the substance contained therein, the heating including applying an electrical current to the mesh containing the substance for a predetermined amount of time for neutralizing or reducing an effectiveness of the substance.

14. The computer usable program product of claim 13, wherein determining whether the user is authenticated is performed by a radio frequency identification (RFID) circuit of the delivery device.

15. The computer usable program product of claim 13, wherein heating of the substance comprises discharging a capacitor into a mesh configured to encapsulate the substance.

16. The computer usable program product of claim 13, wherein the program instructions are stored in the at least one computer readable storage device in a data processing system, and wherein the program instructions are transferred over a network from a remote data processing system.

17. The computer usable program product of claim 13, wherein the program instructions are stored in the at least one computer readable storage device in a server data processing system, and wherein the program instructions are downloaded over a network to a remote data processing system for use in a computer readable storage device associated with the remote data processing system.

18. A computer system comprising one or more processors, one or more computer-readable memories, and one or more computer-readable storage devices, and program instructions stored on at least one of the one or more storage devices for execution by at least one of the one or more processors via at least one of the one or more memories, the stored program instructions comprising:
   program instructions to monitor, by a circuit of a delivery device, for receiving an authentication signal, the delivery device containing a substance encapsulated in a mesh;
   program instructions to determine whether a user is authenticated based upon the authentication signal and an identifier stored within the delivery device; and
   program instructions to cause heating, responsive to determining that the user is not authenticated within a predetermined time period after the delivery device being ingested by the user, the mesh and the substance contained therein, the heating including applying an electrical current to the mesh containing the substance for a predetermined amount of time for neutralizing or reducing an effectiveness of the substance.

* * * * *